United States Patent [19]

Howard et al.

[11] Patent Number: 4,984,452
[45] Date of Patent: Jan. 15, 1991

[54] MULTIPLE CHANNEL AUTOMATIC CONCENTRATION METER

[75] Inventors: Robert G. Howard, Annapolis; Edwin L. Zivi, Jr., Severna Park, both of Md.

[73] Assignee: The United States of America as represented by the Secretary of the Navy, Washington, D.C.

[21] Appl. No.: 921,622

[22] Filed: Jun. 27, 1978

[51] Int. Cl.$^5$ .................. G01N 25/00; G01N 11/00
[52] U.S. Cl. ..................... 73/61.3; 73/61 R; 73/61.1 R
[58] Field of Search ............ 73/15 A, 25, 27, 61 R, 73/61.1 R, 190 H, 190 R, 61.3, 61.1, 61

[56] References Cited

U.S. PATENT DOCUMENTS

| | | | |
|---|---|---|---|
| 2,779,189 | 1/1957 | Corneil | 73/61 R |
| 3,256,734 | 6/1966 | Storke | 73/190 H |
| 3,548,637 | 12/1976 | Wicks | 73/53 |
| 3,648,516 | 3/1972 | McRonald | 73/190 H |
| 3,712,116 | 1/1973 | Andre | 73/61.1 R |
| 3,726,126 | 4/1973 | Vittorio | 73/190 R |
| 3,924,448 | 12/1975 | Howard et al. | 73/61.1 R |
| 4,062,223 | 12/1977 | Lamphere et al. | 73/61.1 R |
| 4,140,396 | 2/1979 | Allington | 73/190 R |

Primary Examiner—Nelson Moskowitz
Attorney, Agent, or Firm—Luther A. Marsh

[57] ABSTRACT

This system measures the concentration level of additives dissolved or suspended in a liquid by measuring the changes which the additives cause to the heat transfer characterisitics of the liquid. A plurality of cylinders and pistons sample the liquid to be measured and pump the samples past a hot film anemometer probe at a constant flow rate. A grid of wires upstream from the hot film anemometer probe is used to cause isotropic turbulence in the liquid flow around the measuring probe. The output signal from the measuring probe is proportional to the rate at which heat is transferred away from the probe by the liquid flowing past. The rate at which heat is transferred away from the probe is a function of the specific heat, thermal conductivity, viscosity, and turbulent flow characteristics of the liquid which in turn are a function of the concentration level of additives in the liquid. Calibration curves for a given additive, liquid temperature and liquid flow rate are used to determine concentration level from the measurement probe output signal.

10 Claims, 3 Drawing Sheets

MULTIPLE CHANNEL AUTOMATIC CONCENTRATION METER

The invention described herein may be manufactured and used by or for the Government of the United States of America for governmental purposes without the payment of any royalties thereon or therefor.

BACKGROUND OF THE INVENTION

The prior art discloses systems which measure differences in concentration levels of additives in a liquid or differences between two different liquid mixtures by measuring the heat capacity or the thermal conductivity of the liquids. Prior art systems measure the heat capacity of a liquid by measuring the temperature rise of the liquid as it flows past a heating element at a constant flow rate. Thermisters have been used in the prior art to provide an output signal which is a function of the specific heat, thermal conductivity and flow rate of the liquid flowing past them. Electrical current flowing through the thermisters heat them above the ambient temperature of the liquid flowing past. Since the liquid flow past the thermisters tends to cool them down, the temperatures of the thermisters reach equilibrium values which are proportional to the rate at which the heat is being transferred away from them by the flowing liquid. The output current of the thermisters are proportional to their internal resistance which in turn is proportional to this equilibrium temperature. Hot wire and hot film anemometers operate on the same principles as do thermisters and are frequently used to measure flow rates of fluids. In anemometers, a hot wire or hot film on the probe of the anemometer is heated by electrical current to a temperature above the ambient temperature of the fluid flowing past it, the internal resistance of this hot wire or film being proportional to its temperature.

The prior art teaches the use of thermisters and anemometers to detect changes in the thermal properties of liquids caused by additives in the liquids. However, these prior art systems have several limitations. Several of the prior art measurement systems do not maintain a constant flow rate past the thermister or anemometer and therefore are unable to distinguish between changes in flow rate and changes in the concentration level of additives in the liquid. None of the prior art measurement systems includes a means for sampling liquid from several different sources and sequentially measuring the additive concentration level in these different samples using a single sensor. The output signals of hot film anemometers or thermisters will also vary as a function of the ambient temperature of the liquid flowing past them, but none of the prior art measurement systems include means to compensate the output signals to remove the effects of changing liquid ambient temperature. The prior art measurement systems could not be used to measure the concentration level of additives in a liquid which change the viscosity, thickness of the laminar boundary layer or other turbulent flow characteristics of the liquid without changing the specific heat and heat conductivity of the liquid. The effects of such additives on the output signal of prior art system are very indirect and unpredictable.

SUMMARY OF THE INVENTION

This measurement system uses a plurality of hydraulic cylinders, pistons and valves to draw samples of the liquid to be measured from many different locations and to cause these liquid samples to flow sequentially through a measurement chamber at a constant velocity. The measurement chamber and the associated electronic circuits measure the parts per million concentration level of a known additive, either dissolved or suspended in the liquid. As the liquid flows at a constant velocity through the entrance of the measurement chamber, it flows through a grid of closely spaced wires which produces isotropic turbulence in the liquid flow. The measurement probe of a hot film anemometer is placed in the turbulent liquid flow downstream from the grid of wires. As the liquid flows past the measurement probe, it flows with a laminar boundary layer of varying thickness over the surface of the probe. The thickness of this boundary layer is a function of the viscosity and turbulent flow characteristics of the liquid, which in turn are a function of the concentration level of certain types of additives in the liquid. As electrical current flows through the metallic film on the measurement probe of the anemometer and causes the film to heat up above the ambient temperature of the liquid flowing past it, heat will tend to flow away from the film by conduction through the laminar boundary layer and by convection through the turbulent flow regions outside of the laminar boundary layer. Since the heat is transferred at a much lower rate by conduction through the laminar boundary layer than by convection through the turbulent region outside the boundary layer, the rate at which heat is transferred away from the hot film is proportional to the thickness of the boundary layer. The electrical resistance of the metallic film on the measurement probe increases with increasing temperature. The electronics circuits connected to the measurement probe supply whatever amount of DC current to the probe which may be necessary to keep the electrical resistance and therefore the temperature of the metallic film constant. Therefore, the concentration level of certain types of additives in the liquid flowing past the measurement probe will determine the thickness of the laminar boundary layers surrounding the probe which in turn will determine the rate at which heat is transferred away from the probe and the amount of current flowing through the metallic film. The ambient temperature of the liquid flowing past the probe is measured and used to adjust the current output of the probe so that the measured values of concentration level will be independent of the temperature of the liquid.

A principle objective of this invention is to overcome the deficiencies of the prior art measurement systems. Other objectives of this invention are to provide a system for measuring concentration levels of additives in a liquid which compensates for changes in the ambient temperature of the liquid being measured, which maintains a constant liquid flow rate while the liquid is being measured, which can take several different samples of the liquid at different locations and sequentially measure these samples, and which can measure the concentration levels of additives in the liquid which change the viscosity, thickness of the laminar boundary layer or other turbulent flow characteristics of the liquid without changing the specific heat and thermal conductivity. Additional objectives of the invention are to provide a measurement system which is easy and convenient to operate and which can take fast and reliable measurements.

DESCRIPTION OF THE PREFERRED EMBODIMENT

The preferred embodiment of this invention was built and tested by the inventor for the purpose of measuring the concentration levels of additives in water which affect the viscosity and turbulent flow characteristics of the water. This invention may also be used to measure concentration levels of additives which change the specific heat or thermal conductivity of water and to measure concentration levels in liquids other than water. The only conditions required for the use of this invention are that the additives in the liquid must change either the specific heat, thermal conductivity, viscosity or turbulent flow characteristics of the liquid or some combination of these variables in a reproducible manner. These changes must be proportional to concentration.

Figure 1:
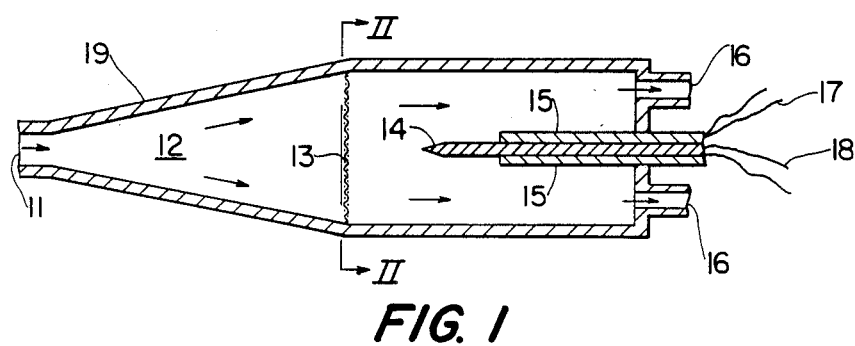
FIG. 1 is a cross-sectional view of the measurement chamber including the measurement probe and the grid of wires producing isotropic turbulence.
Figure 2:
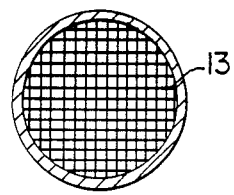
FIG. 2 shows another cross-sectional view of the measurement chamber taken perpendicular to the cross-sectional view of FIG. 1.

FIG. 1 shows a cross-sectional view of the measurement chamber 19, which includes the measurement probe 14. The measurement probe 14 is shown in more detail in the pictorial view of FIG. 3, and the means for producing isotropic turbulence 13 in the measurement chamber 19 is shown in more detail in the cross-sectional view of FIG. 2. The liquid is caused to flow at a constant velocity through the intake 11 of the measurement chamber 19, through the cone shaped diffuser 12 and the wire grid 13. In the preferred embodiment, the wire grid 13 comprises a large number of very small wires spaced 0.06 inches apart in a rectangular pattern as shown in FIG. 2. This wire grid causes isotropic turbulence in the liquid flow on the downstream side of the grid. The turbulence in a fluid is defined to be isotropic if the time averaged magnitudes of the fluctuating components of velocity are approximately equal in all directions. The liquid will flow through the measurement chamber from left to right as indicated by the arrows and flow past the measurement probe 14 at a constant average velocity. The turbulence velocity vectors of the fluid flow will be superimposed on top of the average velocity vector of the fluid flow through the chamber from left to right. The liquid exits from the measurement chamber through the drain 16 which is annular in shape and is positioned concentric with the measurement probe 14. The measurement probe 14 is positioned in the center of the measurement chamber immediately downstream from the wire grid 13. Surrounding the measurement probe 14 is the temperature compensation probe 15 which is in the shape of a cylinder mounted coaxial with the measurement probe. The wires 17 from the temperature compensation probe 15 and the wires 18 and the measurement probe 14 provide the output signals to the circuit shown in FIG. 5.

Figure 3:
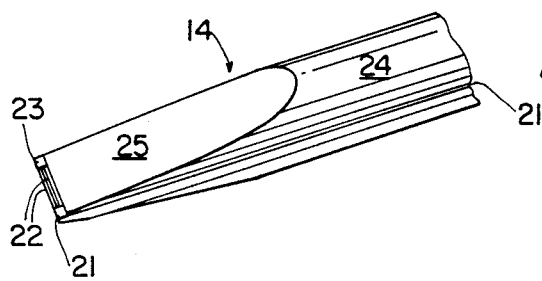
FIG. 3 is a pictorial view of the measurement probe.

The enlarged pictorial view in FIG. 3, shows that the measurement probe 14 has a main cylindrical portion 24 and an end portion 25 which is wedge shaped. The wire leads 18 are mounted on the measurement probe 14 in the form of two metal strips. The strips 21 and 23 connect the sensing element 22 to the other components of the wheatstone bridge. Strip 21 extends along one side of the probe towards the sensing element 22 and strip 23 extends along the opposite side (not shown) of the probe. The sensing element 22 located at the tip of the wedge 25 connects the two leads 21 and 23. The body of the probe is made of an insulating material such as quartz. The leads 21 and 23 and sensor element 22 are made of noncorroding, highly conductive metals such as gold and platinum. The temperature compensation probe 15 comprises a coil of wire wound around the measurement probe 14 and embedded in an insulating material.

Figure 5:
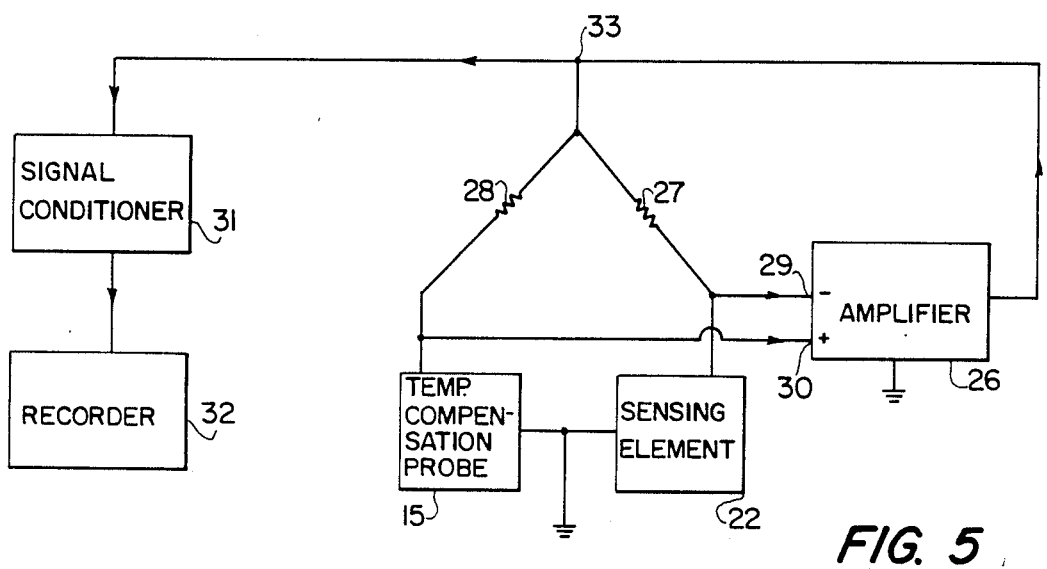
FIG. 5 is a block diagram of an electronic circuit for use in the system of measurement of this invention.

As shown in the block diagram of FIG. 5, the sensing element 22 of the measurement probe 14 and the temperature compensation probe 15 form two legs of a wheatstone bridge which also includes the resistors 27 and 28. There will always be some current flowing through the sensing element 22 and temperature compensation probe 15. The size and internal resistance of the sensing element 22 is set so that the current flowing through it will heat the sensing element to a temperature considerably above the temperature of the liquid flowing through the measurement chamber. The internal resistances of the measurement probe and the temperature compensation probe are directly proportional to the temperature of the probes. As the liquid flowing past the measurement probe causes heat to be transferred away from the probe, the temperature of the measurement probe will tend to decrease and cause the resistance of the probe to decrease. Any decrease in the resistance of the sensing probe will decrease the voltage at the input 29 of the amplifier 26. The amplifier 26 is set so that when the voltage at the input 29 decreases, the current output will increase and cause the current through resistor 27 and sensing element 22 to increase also. This feedback loop will tend to keep the voltage at input 29 of amplifier 26 equal to the voltage at input 30. The coil of wire in the temperature compensation probe 15 is constructed so that the current flowing through it in the circuit of FIG. 5 will not heat the temperature compensation probe significantly above the temperature of the liquid flowing past. Therefore, the internal resistance of the temperature compensation probe 15 will increase or decrease only to the extent that the temperature of the liquid flowing past increases or decreases. Since the coiled wire in the temperature compensation probe 15 is coated, the probe 15 will not respond to temperature fluctuations as fast as the sensing element 22 but will tend to smooth the fluctuations out. Whereas the ratio of the resistances of resistor 27 and sensing element 22 will tend to rise or fall in response to any variable which affects the rate of heat transfer away from the measurement probe 14, the ratio of the resistances of resistor 28 and temperature compensation probe 15 will rise or fall only in response to changes in the temperature of the liquid flowing through the measurement chamber 19. Because the inputs 29 and 30 to the amplifier 26 are of opposite polarity, the effects of temperature changes in the liquid are cancelled out.

Figure 4:
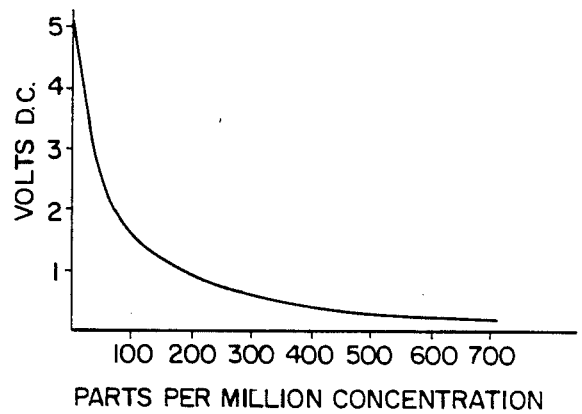
FIG. 4 shows a typical calibration curve.

FIG. 4 illustrates how the voltage across the wheatstone bridge between point 33 and the ground will vary as a function of the concentration level of a typical additive which has the effect of reducing the rate at which heat is transferred away from the sensing element 22 through the liquid. Such an additive may be dissolved in the liquid or may comprise suspended particles in the liquid. Any additive which has the effect of increasing the rate at which heat is transferred away from the sensing element 22 will cause the voltage at point 33 to increase with increasing concentration levels instead of decreasing as is illustrated in FIG. 4. A voltage output curve similar to that shown in FIG. 4 could be produced by additives which reduce the specific heat or the thermal conductivity of a liquid. Such an output curve could also be produced by additives which increase the viscosity of a liquid or increase the thickness of the laminar boundary layer of liquid formed around the surface of the measurement probe as the liquid flows past it.

Heat is transferred at a much lower rate by conduction through the laminar boundary layer surrounding the measurement probe than it is by convection through the turbulent flow regions outside of this boundary layer. Because the heat transfer through the laminar boundary layer is by conduction and the heat transfer outside of the boundary layer is by convection, the rate at which heat is transferred away from the sensing element 22 will be directly proportional to the thickness of the laminar boundary layer surrounding the probe. A means for producing isotropic turbulence, such as the wire grid 13, is needed in the measurement chamber to ensure that the liquid flow outside of the boundary layer immediately surrounding the measurement probe will have a constant reproducible level of turbulence. To obtain a constant level of isotropic turbulence surrounding the measurement probe, it is also desirable to maintain the average velocity of liquid flow through the chamber constant and to make the shape of the measurement chamber symmetrical about the measurement probe. Another technique that can be used along with the wire grid to create uniform turbulence around the measurement probe is to flow the liquid through a relatively long length of passageway before entering the measurement chamber with the size and cross-section of the passageway uniformly equal to that of the entrance to the measurement chamber.

The signal conditioner 31 filters the noise out of the voltage signal at point 33 and, if desired, converts this analog signal into digital form. The final output signal may be recorded on a recorder 32 or displayed on any number of display means well known to those skilled in the electronics arts. The wheatstone bridge, the amplifier 26, and a signal conditioner 31 may be referred to as a means for processing the output signal of the measurement probe. Before using this system to measure the concentration level of a particular additive in a particular liquid, it is necessary to obtain a calibration curve, such as the one in FIG. 4, so that the concentration level can be derived from the voltage output readings.

Figure 6:
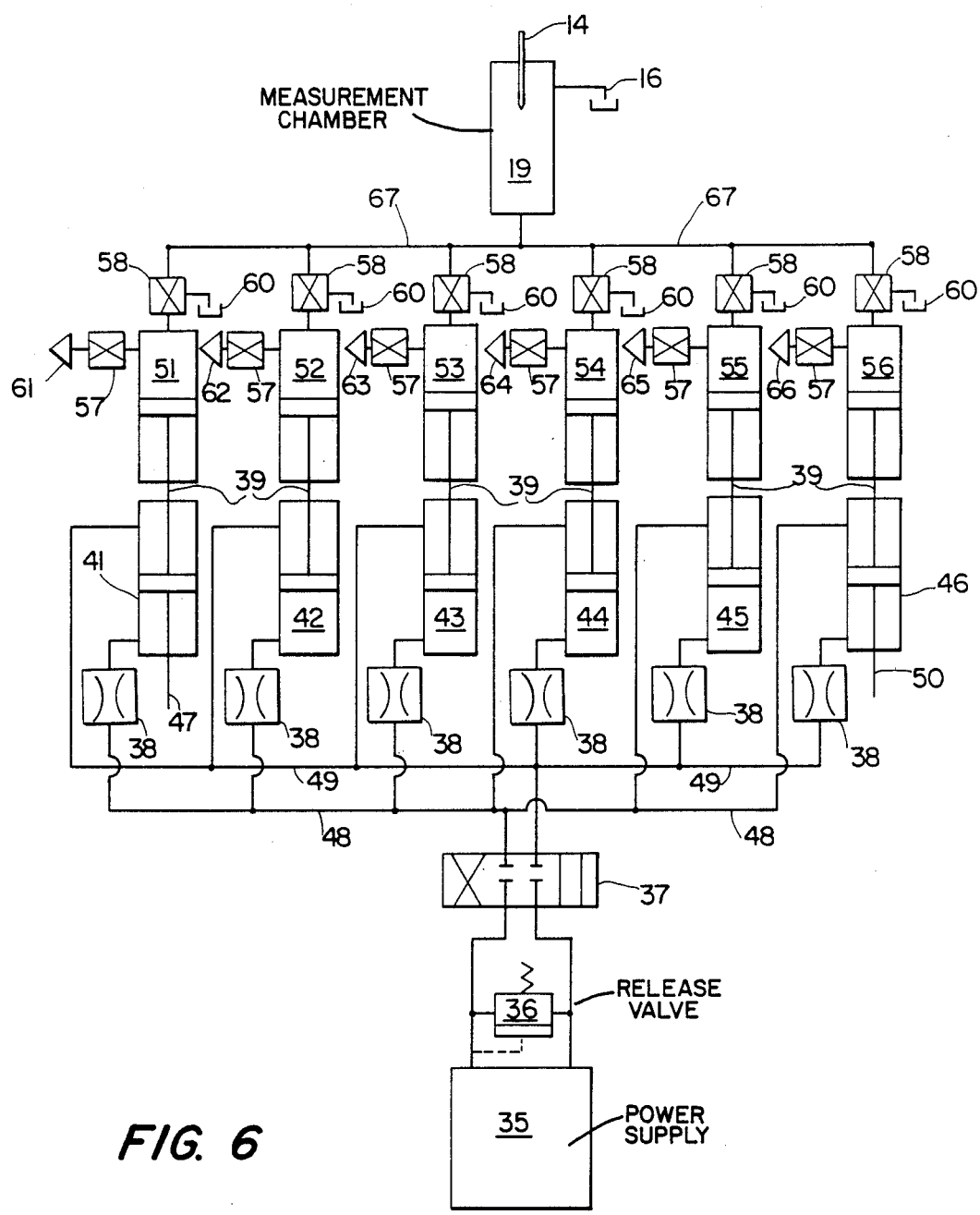
FIG. 6 is a schematic diagram of the hydraulic system for sampling the liquid to be measured.
Figure 7:
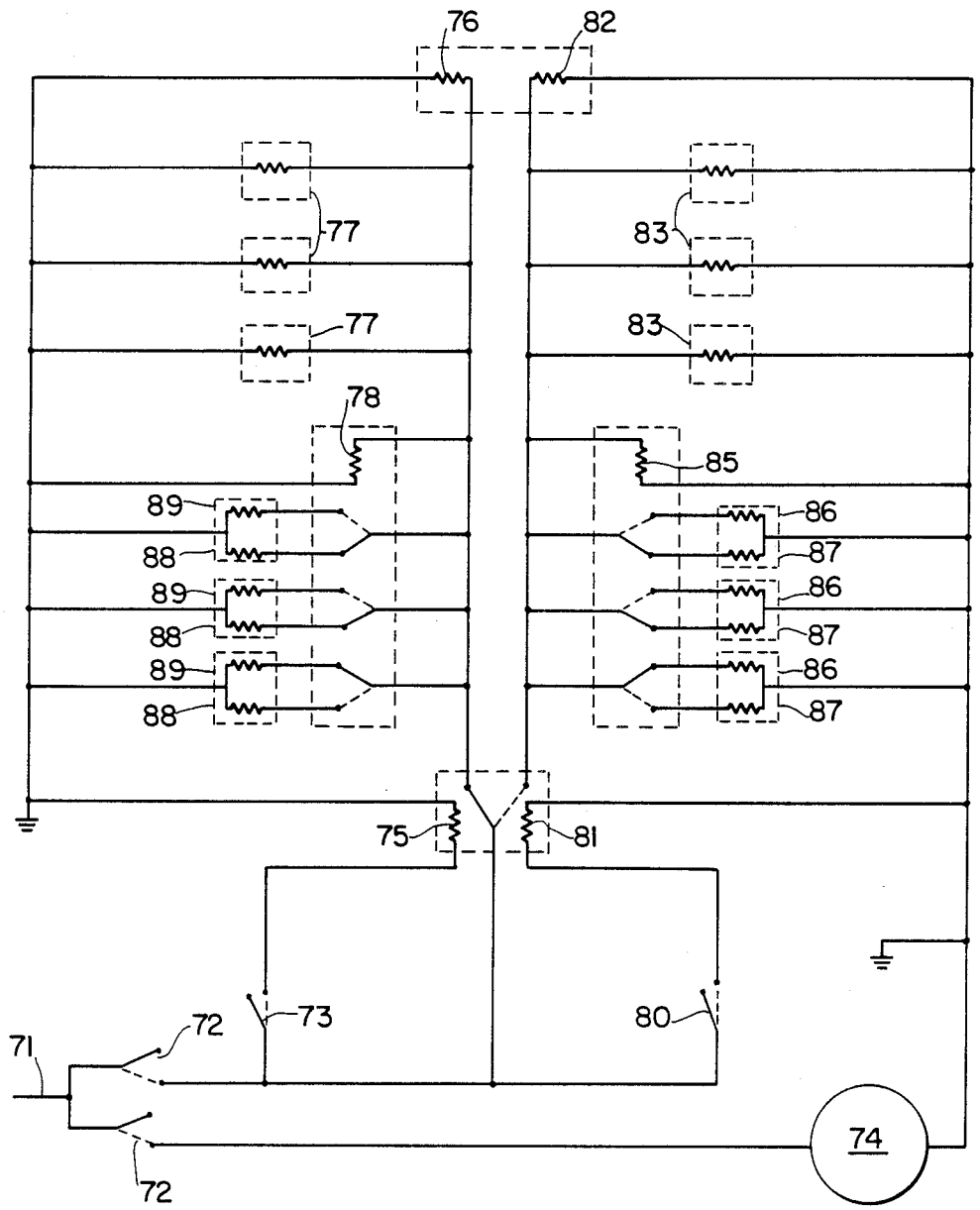
FIG. 7 is an electrical schematic diagram showing the control circuit for controlling the operation of the hydraulic network.

The proper operation of this measurement system requires that the liquid flows through the measurement chamber at a constant rate. Any device capable of producing such a constant flow may be used for this system. One example of such a flow producing means is illustrated in FIGS. 6 and 7. In FIG. 6 is shown a hydraulic power supply 35 which contains an oil reservoir and an electrically powered pump. A pressure release valve 36 is installed across the input and output lines of the power supply 35. A four-way hydraulic valve 37 is used to turn on and off the flow of oil and to reverse the direction of flow in the two hydraulic lines 48 and 49. Six hydraulic actuating cylinders 41–46 contain pistons which are attached by means of piston rods 39 to sampling pistons in the six sampling cylinders 51–56. The hydraulic lines 49 and 48 are connected to the four-way valve 37 and to the actuating cylinders in such a way that the pistons within cylinders 41, 42, and 43 will move up while the pistons within cylinders 44, 45, and 46 move down and vice versa. The flow controls 38 limit the rate at which hydraulic oil can enter or leave the lower portions of the actuating cylinders 41–46 so that the pistons and piston rods 39 will be reciprocating at a constant rate. The pistons in the sampling cylinders 51–56 draw in samples of liquid through ports 61–66 and associated valves 57. These liquid samples leave the sampling cylinders through three-way valves 58 which direct the samples either to the drains 60 or through the line 67 to the measurement chamber 19 where the liquid flows past the measurement probe 14 and into the drain 16.

The circuit illustrated in FIG. 7 is used to control the opening and closing of the valves 37, 57, and 58 in the hydraulic system shown in FIG. 6. Electrical power is applied at point 71 through the main on-off power switch 72 and is supplied to the hydraulic pump 74. The extension 47 of the piston rod in the actuating cylinder 41 closes the limit switch 80 when the piston reaches the top of the cylinder. The extension 50 of the piston rod in the actuating cylinder 46 closes the limit switch 73 whenever the piston reaches the top of the cylinder. The pistons in the actuating cylinders 41, 42, and 43 reach the top of their cylinder at the same time that the pistons in the actuating cylinders 44, 45, and 46 reach the bottom of their cylinders. When the piston in actuating cylinder 41 reaches the top of the cylinder and the limit switch 80 is closed, the latching relay coil 81 is activated causing the electrical power to be switched from the left side of the circuit shown in FIG. 7, to the right side. Power is then applied through coil 82, which switches the four-way valve 37. This reverses the direction of flow of hydraulic oil through lines 48 and 49 so that the pistons in actuating cylinders 41, 42, and 43 will begin to move down while the pistons in actuating cylinders 44, 45, and 46 will begin to move up. At the same time, the three coils 83 are activated to cause the normally closed valves 57, attached to sampling cylinders 51, 52, and 53, to open. Also at the same time, power is applied to the coils 86 and 87 to open the valves 58 attached to the sampling cylinders 54, 55, and 56 so that liquid flowing from these cylinders may pass to either the measurement chamber 19 or to the drains 60. When the piston in cylinder 46 reaches the top of its cylinder, the limit switch 73 will be closed to activate the coil 75 of the latching relay and cause the electrical power to be switched from the right side of the circuit in FIG. 7 to the left side. After the power is switched in this way, the coil 76 will be activated which will switch the position of the four-way valve 37. This will reverse the direction of the flow of oil through the hydraulic lines 48 and 49 so as to cause the pistons in the actuating cylinders 44, 45, and 46 to begin moving down and the pistons in the actuating cylinders 41, 42, and 43 to begin moving up again At the same time the normally closed valves 57, attached to the sampling cylinders 54, 55, and 56, will be open by the coils 77 to allow a fresh sample of liquid to be drawn into the cylinders. Also at the same time, the normally closed valves 58, attached to sampling cylinders 51, 52, and 53, will be opened to allow the contents of those cylinders to exit either to the line 67 and measurement chamber 19 or to the drains 60. Thus it can be seen that at all times three of the sampling cylinders will be flushing out their liquid contents either to the drains 60 or through the line 67 to the measurement cylinder 19 while the other three cylinders are drawing in a new sample of liquid. In this manner the flow producing means illustrated in FIG. 6 is able to produce a constant flow of liquid through the measurement chamber.

The three-way valves 58 are used as a means for selectively directing the flow of liquid past the measurement probe from only one of the sampling cylinders at a time and causing the liquid from the other cylinders to be diverted to the drains. The three-way stepping switches 78 and 85 and the coils 86, 87, 88, and 89 are used as a means for selecting which one of the sampling cylinders at any particular time will provide liquid to flow past the measurement probe. The three coils 88 are used to open the normally closed three-way valves 58, attached to sampling cylinders 51, 52, and 53, so as to allow the liquid to flow through the valves to the drains 60. The three coils 89 are used to open the same set of three-way valves 58 so as to allow liquid from cylinders 51, 52, and 53 to pass through the valves to the measurement chamber. In a similar manner, the three coils 87 are used to open the normally closed three-way valves 58, attached to the sampling cylinders 54, 55, and 56, to allow liquid to pass through to the drains 60. The three coils 86 are used to open the same set of three-way valves 58 to allow liquid to flow through them to the measurement chamber. The three-way stepping switch 78 allows only two of the coils 88 and one of the coils 89 to be activated at any one time. Therefore, at any time when the three valves 58 controlled by switch 78, are activated to an open position, two of them will be open to drain 60 and only one of them will be open to the measurement chamber 19. Every time the limit switch 73 is closed causing the latching relay 75 to reactivate the stepping switch 78, the switch 78 will cycle to open a different one of the three-way valves 58 to the measurement chamber with the other two three-way valves 58 opened to the drain. The stepping switch 85 and the coils 86 and 87, which control the three-way valves 58 attached to the sampling cylinders 54, 55, and 56, operate in the same way. Thus it can be seen that the contents of each one of the sampling cylinders successively be pumped through the measurement chamber 19 on every third cycle of the pistons within the cylinders and will be diverted to the drain on the other two cycles. Obviously it would be possible to have more or less than three sampling cylinders in each of the two banks of cylinders.

This invention may be used to measure concentration levels of any additive which changes the thickness of the laminar sublayers of the liquid flowing past the measuring element. In the preferred embodiment of this invention, this laminar sublayer thickness is determined by measuring the rate at which heat is transferred away from a measurement probe through the sublayers. Other methods of measuring the sublayer thickness may also be used which are not related to the thermal properties of the liquid. However, regardless of the method used to measure laminar sublayer thickness, the conditions under which the sublayers are formed near the measuring element must be carefully controlled. The average velocity of liquid flow past the measuring element and the amount of turbulence in the liquid are two factors that must be controlled. The approach taken in the preferred embodiment of this invention is to maintain the flow velocity and the turbulence at reproducible constant levels. The output signals of the laminar sublayer measuring device are then calibrated with respect to those constant flow and turbulence levels.

Although the preferred embodiment of this invention described above used a hot film anemometer, a hot wire anemometer and other similar sensors could also be used if appropriately mounted within the measurement chamber. A separate sensor was used to measure the temperature of the liquid flowing through the measurement chamber in the described embodiment and the output signal from this sensor was used to adjust the output from the heat transfer measurement sensor to compensate for the effects of changing liquid temperatures. If the liquid temperatures could somehow be held constant, this compensation would be unnecessary. Even when the temperature of the liquid is not constant, those skilled in the art will recognize that there are many other ways to compensate the output signal of the heat transfer measurement sensor so as to remove the inaccuracies which might occur in the measurement as a result of changing the liquid temperatures. Obviously, many other modifications and variations of this invention are possible in light of the above teachings. It is therefore to be understood that within the scope of the appended claims the invention may be practiced otherwise than as specifically described.

What is claimed is:

1. A system for measuring the concentration level of additives in a liquid comprising:
   a measurement probe having means for heating a portion of the probe above the temperature of the liquid and for producing an output signal whose magnitude is proportional to the rate at which heat is transferred away from the heated portion of said probe;
   a flow producing means for maintaining a flow of said liquid past said probe at a constant velocity while said concentration levels are being measured;
   means for producing isotropic turbulence in the flow of said liquid past said probe; and
   means for processing the output signal from said probe to derive the concentration level of said additives in said liquid.

2. The system of claim 1 wherein said means for heating a portion of said probe and for producing an output signal comprises an electrically conductive sensing element on the surface of said probe with the sensing element rising in temperature when current is transmitted through it, the electrical resistance of the sensing element being proportional to it's temperature, and with the output signal from the probe being a function of said resistance.

3. The system of claim 1 wherein said means for producing isotropic turbulence in the liquid flow past said probe comprises a grid of wires placed in the path of the flowing liquid upstream from the probe.

4. The system of claim 2 wherein said means for producing isotropic turbulence in the liquid flow past said probe comprises a grid of wires placed in the path of the flowing liquid upstream from the probe.

5. The systems of claims 1, 2, 3, and 4, wherein said flow producing means comprises a plurality of cylinders containing reciprocating pistons which alternately draw the liquid into the cylinders and then force the liquid out of the cylinders and past said probe at a constant velocity.

6. A system for measuring the concentration level of additives in a liquid comprising:
   a measurement probe having means for generating heat and generating an output signal proportional to the rate at which heat is transferred away from the probe;
   means for processing the output signal from said probe to derive the concentration level of said additive;
   a flow producing means for maintaining a flow of the liquid past said probe at a constant velocity while said concentration levels are being measured, said means comprising a plurality of cylinders containing reciprocating pistons which alternately draw the liquid into the cylinders and then force the liquid out of the cylinders and past said probe.

7. The system of claim 6 wherein said flow producing means further comprises:
   means for selectively directing the flow of liquid past said probe from only one cylinder at any time with the liquid from the other cylinders being diverted elsewhere;
   means for selecting which one of the cylinders at any particular time will provide liquid to flow past said probe; and
   means for causing the cylinders to draw liquid samples from different locations and for causing the liquid samples to be measured in any desired sequential order.

8. A method for determining the concentration level of additives in a liquid comprising the steps of:
   flowing the liquid past a measuring element at a constant velocity;
   introducing isotropic turbulence in the liquid flow around the measuring element;
   heating the measuring element to a temperature above the ambient temperature of the liquid flowing around it;
   measuring the rate at which heat energy is transferred away from the measuring element; and
   computing the additive concentration level from the measured heat transfer rate.

9. A method for determining the concentration level of additives in a liquid comprising the steps of:
   flowing the liquid past a measuring element at a constant velocity and turbulence level;
   measuring the thickness of the laminar sublayer of the liquid flowing by the measuring element; and
   computing the additive concentration level from the measured laminar sublayer thickness.

10. The method of claim 9 wherein the thickness of said laminar sublayer is measured by measuring the rate at which heat energy can be transferred through the sublayer.

* * * * *